Figure 1:
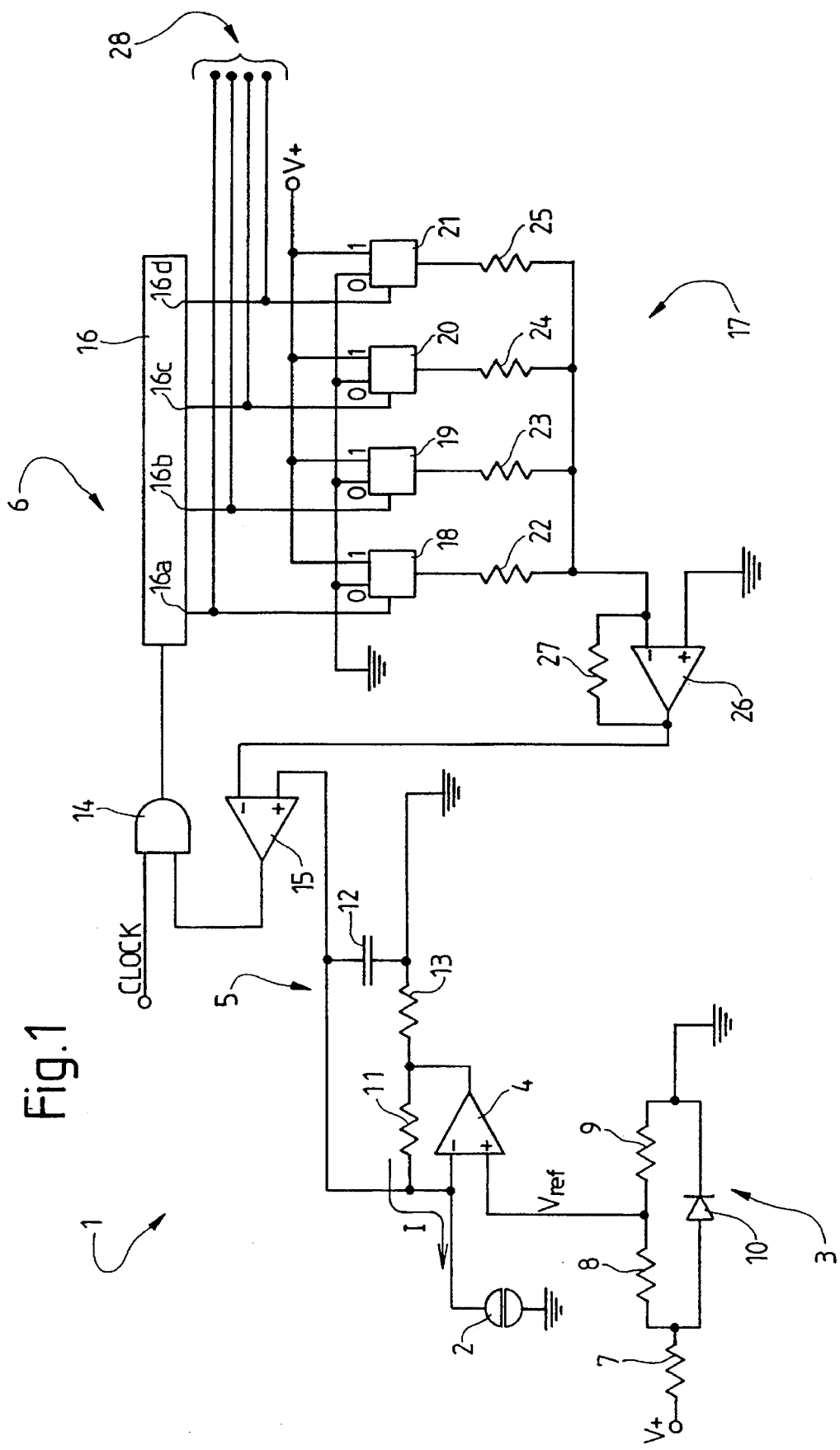

United States Patent [19]
Wiget

[11] Patent Number: 5,532,602
[45] Date of Patent: Jul. 2, 1996

[54] DIAGNOSTIC CIRCUIT AND METHOD FOR AMPEROMETRICALLY DETERMINING THE CURRENT PASSING THROUGH A SENSOR

[75] Inventor: Fridolin Wiget, Neuchâtel, Switzerland

[73] Assignee: Asulab S.A., Bienne, Switzerland

[21] Appl. No.: 263,070

[22] Filed: Jun. 21, 1994

[30] Foreign Application Priority Data

Jun. 22, 1993 [FR] France ................... 93 07674

[51] Int. Cl.⁶ ............................................. G01R 27/02
[52] U.S. Cl. ............................... 324/605; 327/77
[58] Field of Search ........................... 324/605, 705, 324/692, 693, 713, 715; 327/77, 78

[56] References Cited

U.S. PATENT DOCUMENTS

| | | |
|---|---|---|
| 4,215,336 | 7/1980 | Smith. |
| 4,277,697 | 7/1981 | Hall et al. ............... 327/77 |
| 4,420,564 | 12/1983 | Tsuji et al.. |
| 4,721,865 | 1/1988 | Tallaron et al. .......... 327/77 |
| 4,906,055 | 3/1990 | Horiuchi ................. 327/77 |
| 5,027,328 | 6/1991 | Nakashima ............... 327/77 |
| 5,030,850 | 7/1991 | Lunsford ................. 327/77 |
| 5,245,526 | 9/1993 | Balakrishnan et al. .... 327/77 |
| 5,304,865 | 4/1994 | Schoofs ................. 327/77 |
| 5,336,944 | 8/1994 | Fischer ................. 327/77 |
| 5,347,224 | 9/1994 | Brokaw ................. 327/77 |

FOREIGN PATENT DOCUMENTS

| | | |
|---|---|---|
| 471986 | 2/1992 | European Pat. Off.. |
| 2200119 | 7/1973 | Germany. |
| 2826723 | 12/1979 | Germany. |

OTHER PUBLICATIONS

"Temperaturemessung mit linearisierten NTC–Netzwerken und Umsetzung in Impulsfolgen", Messen & Prufen, No. 4, Apr. 1979, Bad Worishofen de, pp. 255–258.

*Primary Examiner*—Maura K. Regan
*Attorney, Agent, or Firm*—Sughrue, Mion, Zinn, Macpeak & Seas

[57] ABSTRACT

The invention concerns a diagnostic circuit for amperometrically determining the current passing through a sensor (41). The circuit comprises a current source (V+, 46) for passing a constant DC current through said sensor (41), switching means (45) for selectively operating said current source, comparing means (42) for comparing the potential difference ($V_{BS}$) across said sensor to a reference voltage ($V_{ref}$), and producing a control signal (D) control means (44) for controlling said switching means (45) in response to said control signal (D), and timing means (48,49) for measuring the cumulative time during which said switching signal (Q) has said first logic level during a selected time interval, so as to provide an output signal (50) indicative of a mean value of current ($I_{bs}$ave) passing through said sensor (41).

13 Claims, 3 Drawing Sheets

DIAGNOSTIC CIRCUIT AND METHOD FOR AMPEROMETRICALLY DETERMINING THE CURRENT PASSING THROUGH A SENSOR

This invention relates generally to amperometric circuits and methods of analysis, and more particularly diagnostic circuits and methods of analysis for amperometrically determining the current passing through a sensor. The invention is suitable for use in amperometric analysis using a disposable electroanalytical sensor for the quantitative determination of biological compounds such as glucose from body fluids, and it will be convenient to hereinafter disclose the invention in relation to that exemplary application. It is to be appreciated, however, that the invention is not limited to that application.

Diabetes is a metabolic disease characterised by deficient insulin production by the pancreas which results in abnormal levels of blood glucose. With daily injections of insulin, and strict control of dietary intake, patient's blood sugar level can be properly maintained. However, the blood glucose level must be closely followed in the patient either by clinical laboratory analysis or by daily analysis which the patient can conduct using relatively simple, non-technical methods.

One such method for monitoring a patient's blood sugar level involves the use of sensors comprising at least a reference electrode and a working electrode coated with a mixture of a catalytically active enzyme and a mediator compound (and possibly further coated with a retaining permeable membrane). When such a coated electrode is placed in contact with a substrate containing a substance for which the enzyme exerts a catalytic effect, the mediator compound transfers charge to the electrode. An effective measure of the charge transferred at an certain specified time after the instant of application of a constant potential across the sensor, is found to be proportional to the glucose concentration in the blood sample.

FIG. 1 shows an existing diagnostic circuit 1 for measuring the current passing through such a sensor 2. The diagnostic circuit 1 comprises a reference voltage source 3, an operational amplifier 4, a low-pass filter 5 and an analog/digital converter 6. The reference voltage source 3 comprises three resistors 7, 8 and 9 and a diode 10. The resistor 7 is connected at one end to a voltage supply V+ and at the other end to the anode of the diode 10. The cathode of the diode 10 is connected to a ground supply, whilst the resistors 8 and 9 are connected together in series across the diode 10. The diode 10 thus conducts, the resistors 8 and 9 acts as a voltage divider of the voltage between the terminals of the diode 10 so as to supply a reference voltage $V_{ref}$ of 300 mV to the non-inverting input of the operational amplifier 4.

One electrode of the sensor 2 is connected to the inverting input of the operational amplifier 4, whilst its other electrode is connected to the ground supply. A feedback resistor 11 having a value $R_{11}$ is connected between the output and the inverting input of the operational amplifier 4. The current I flowing in the resistor 11 is thus equal to $V_{ref}/R_{11}$. Due to the virtual ground between the inverting and non-inverting inputs of the operational amplifier 4, the same current I flowing through the resistor 11 also flows through the sensor 2. From knowledge of the value $R_{11}$ of the resistor 11, the value of the current I flowing across the sensor 2 may be determined by measuring the voltage drop across the resistor 11.

The low-pass filter 5 comprises a capacitor 12 and resistor 13, which are connected together in series across the resistor 11 to remove noise or other interference from the voltage signal across the resistor 11.

The analog/digital converter 6 comprises an AND gate 14, a comparator 15, a binary counter 16 and a digital/analog converter 17. The voltage drop across the capacitor 12 is applied to the inverting input of the comparator 15, whilst the output of the comparator 15 is connected to one input of the AND gate 14. A clock signal, referenced CLOCK is supplied to the other input of the AND gate 14 by a convenient timing circuit (not shown). The counter 16 counts output pulses received from the AND gate 14, the number of pulses counted being represented in binary form by the logical state of the its outputs 16a, 16b, 16c and 16d. In this arrangement, the state of the output 16a represents the most-significant-bit and 16d represents the least-significant-bit.

The digital/analog converter 17 comprises four digital switches 18, 19, 20 and 21 each having an control input connected to one of the outputs 16a to 16d of the counter 16 and two inputs respectively connected to ground and to the voltage supply V+. Each of these digital switches 18 to 21 is arranged so that, according to the high or low logic level of the output 16a to 16d to which its control input is connected, its output is connected to either the supply voltage V+ or to ground.

The output of each of the switches 18 to 21 is connected by means of a resistor 22, 23, 24 and 25 respectively to the inverting input of an operational amplifier 26. The non-inverting input of this operational amplifier is connected to the ground and its output is connected both to its inverting input via a feedback resistor 27 and to the inverting input of the comparator 15.

The resistors 22, 23, 24 and 25 have the values R, 2R, 4R and 8R, so that a high at the outputs 16a, 16b, 16c and 16d causes a voltage of 8V, 4V, 2V and V respectively to be applied to the inverting input of the operational amplifier 26 where V is the value of the voltage applied to the inverting input of the operational amplifier 26 when only the output 16d of the counter 16 is in a logically high state. A voltage corresponding to the sum of the voltages applied to its inverting output is provided at the output of the operational amplifier 26. This voltage is compared by the comparator 15 with the voltage across the capacitor 12.

Initially, the counter 16 is set to zero, and each of its outputs 16a, 16b, 16c and 16d is low. The sum of the voltages applied to the inverting input of the operational amplifier 26, and the voltage at the inverting input of the comparator 15, is at zero volts. In these conditions, the output of the comparator 15 is high and the AND gate 14 transmits the clock signal CLOCK to the counter 16. The counter 16 records the number of clock pulses received from the AND gate 14. The binary number at the outputs 16a, 16b, 16c and 16d, representing the number of pulses counted increases linearly with time, is used as the input of the D/A converter 17. The output voltage of the D/A converter 17 increases by steps and has, at each instant, a value corresponding to the sum of the voltages applied to the inverting input of the operational amplifier 26.

As long as the voltage across the capacitor 12 is greater than the voltage at the output of the operational amplifier 26, the output of the comparator 15 is at a high logic level and the AND gate 14 transmits the clock pulses of the signal CLOCK to the counter 16. When the voltage at the output of the operational amplifier 26 exceeds the voltage across the capacitor 12, the comparator output passes to a low logic level, which blocks the AND gate 14 and interrupts the counting of the clock pulses CLOCK. At this moment, the voltage across the capacitor 12 and the voltage at the output of the operational amplifier 26 are approximately equal and the logical states of the outputs 16a, 16b, 16c and 16d of the counter 16 represent a binary number 28, which is a measure of the voltage at the terminals of the capacitor 12. As the value of the resistor 11 is known, the binary number 28 equally representative of the value of the current I passing through the sensor 2.

The diagnostic circuit 1 shown in FIG. 1 is basically analog in nature and requires the use of two operational amplifiers 4 and 26, in addition to the numerous other circuits circuit elements described above, to produce a digital output signal representative of the resistance of the sensor 2. In order to accurately measure the glucose level in the blood sample placed on the sensor, the operational amplifiers 4 and 26 must have excellent DC, small-signal and transient performance and have a highly linear transfer characteristic. In order to achieve such performance, it is often the case that twenty or more transistors as well as several resistive and capacitive circuit elements are required to realise each one of the operational amplifiers 4 and 26. Such designs, which maintain the desired parameters of the amplifier, are also difficult to accurately realise as integrated circuits.

An object of the present invention is to provide a diagnostic circuit for amperometrically determining the current passing through a sensor which alleviates or overcomes the disadvantages of the prior art.

With that object in mind, one aspect of the present invention provides a diagnostic circuit for amperometrically determining the current passing though a sensor, comprising a current source for passing a constant DC current through said sensor, switching means for selectively operating said current source, comparing means for comparing the potential difference across said sensor to a reference voltage and for producing a control signal having a first logic level when said potential difference is less than said reference voltage and a second logic level when said potential difference is greater than said reference voltage, control means for providing a switching signal having said first logic level or said second logic level depending upon said control signal having said first or said second logic level, said switching means being caused to operate when said switching signal has said first logic level, and timing means for measuring the cumulative time passed by said switching signal in the first logic level during a selected time interval, so as to provide an output signal indicative of the mean value of said current passing through said sensor.

A diagnostic circuit is therefore provided in which the number of circuit components is minimized and which does not require the complex and highly accurate circuitry of existing diagnostic circuits. The diagnostic circuit of the present invention is accordingly more easily realised in the form of an integrated circuit.

Another aspect of the present invention provides a method of amperometrically determining the current passing though a sensor using a diagnostic circuit having the current source, switching means, comparing means, control means and timing means described above, characterised in that it comprises the steps of (a) replacing said sensor with a calibration element of known resistance, (b) measuring a first cumulative time passed by said switching signal in said first logic level during said selected time interval so as to determine a calibration factor, (c) replacing said calibration element with said sensor, (d) measuring a second cumulative time passed by said switching signal in said first logic level during said selected time interval, (e) multiplying said second cumulative time by said calibration factor so as to provide an output signal indicative of the mean value of current passing through said sensor.

In this way, the diagnostic circuit may be calibrated so that its output signal is independent of the actual value of current supplied by the constant current source.

The following description refers in more detail to the various features of the present invention. To facilitate an understanding of the invention, reference is made in the description to the accompanying drawings where the diagnostic circuit is illustrated in a preferred embodiment. It is to be understood that the circuit and method of the present invention are not limited to the preferred embodiment as illustrated in the drawings.

Figure 2:
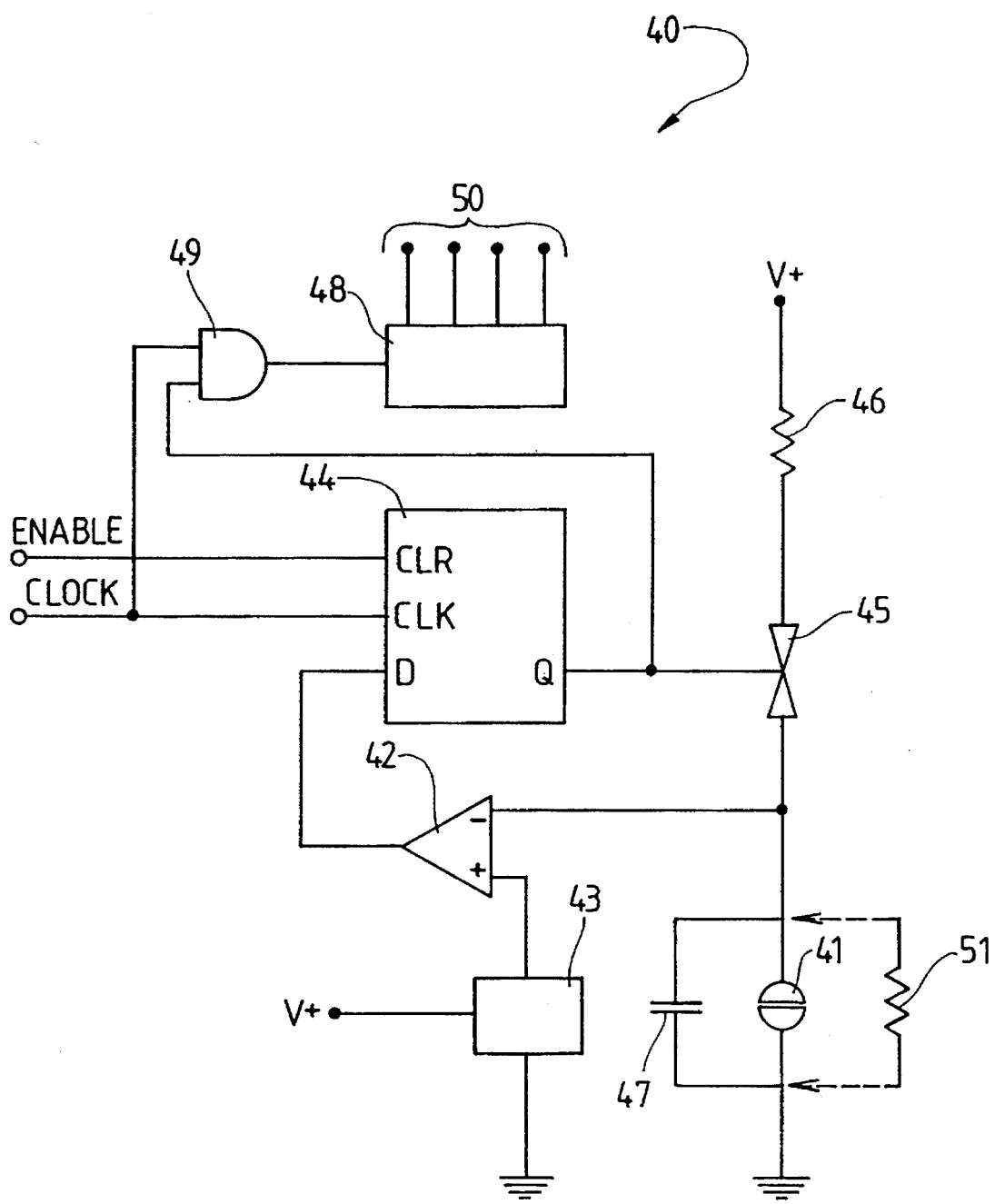
Figure 3:
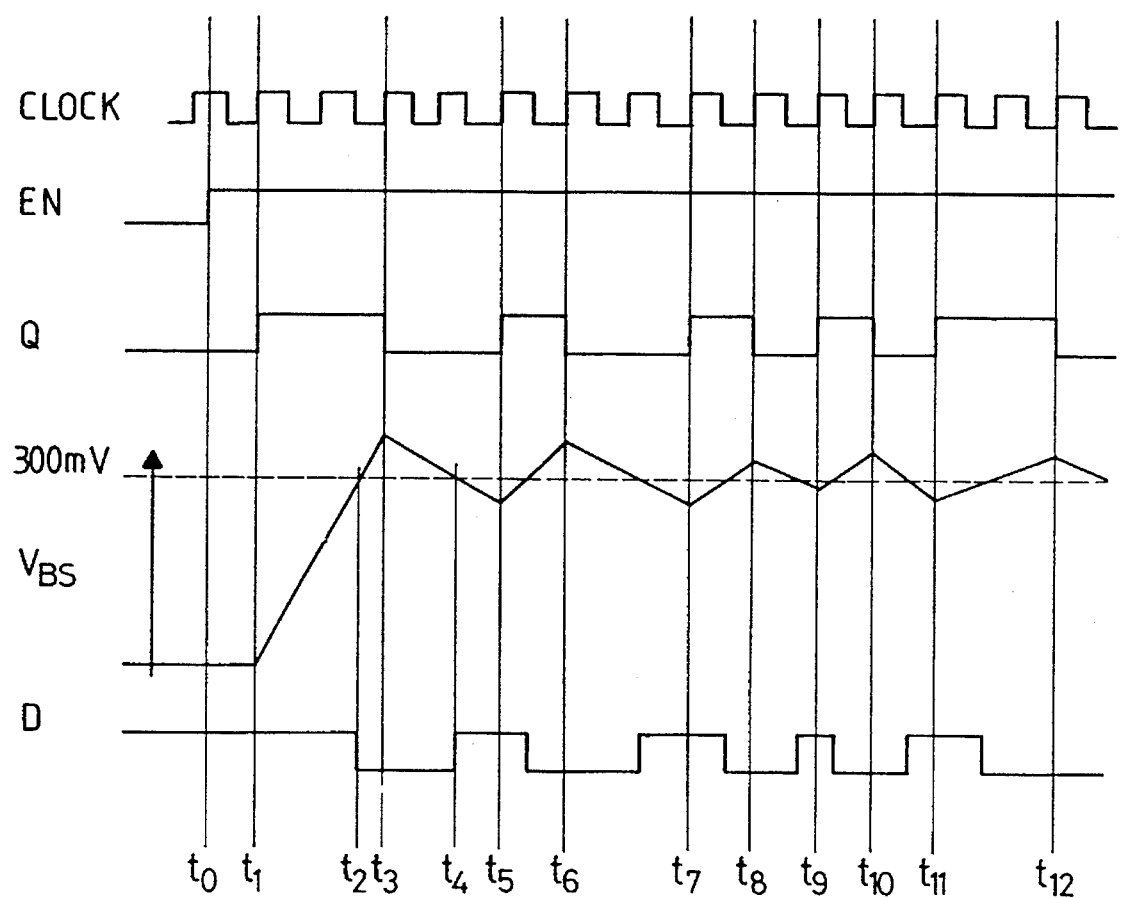

In the drawings:

FIG. 1, already described, is a simplified circuit diagram of an existing diagnostic circuit;

FIG. 2 is a simplified circuit diagram of an embodiment of the diagnostic circuit according to the present invention; and, FIG. 3 is a timing diagram showing the interrelation between various signals of the circuit of FIG. 2.

Referring now to FIG. 2, there is shown generally a diagnostic circuit 40 for amperometrically determining the current passing through a sensor 41. The circuit 40 comprises basically a comparator 42, a reference voltage supply 43, a D-latch 44, an analog gate 45, a load resistor 46, a capacitor 47, a counter 48 and an AND gate 49. The load resistor 46 is connected at one end to a voltage supply V+ and at the other end to the one electrode of the sensor 41 via the analog gate 45. The other electrode of the sensor 41 is connected to a ground supply. The capacitor 47 is connected in parallel across the sensor 41. When the analog gate 45 conducts, current is caused flow through the sensor 41 and the capacitor 47.

The potential difference $V_{BS}$ across the sensor 41 is compared by the comparator 42 to a reference voltage of, for example, 300 mV from the reference voltage supply 43. The output of the comparator 42 is high when the potential difference $V_{BS}$ across the sensor 41 is less than the 300 mV reference voltage and low when the potential difference $V_{BS}$ across the sensor 41 is greater than the 300 mV reference voltage.

The comparator output 42 is connected to the D input of the D-latch 44. A clock signal CLOCK, comprising a series of pulses evenly spaced in time and having, for example, a frequency of 32768 pulses/second, is supplied to the clock input CLK of the D-latch 44. The Q output of the D-latch 44 takes, at the end of each clock pulse CLOCK, the high or low logic level of the signal supplied to the D input at the start of that clock pulse. The state of the Q output is maintained between consecutive clock pulses.

The D-latch 44 also has a reset input, to which is supplied an enable signal ENABLE by a control circuit (not shown in FIG. 2). When the enable signal is low, the Q output of the D-latch 44 is held low. Conversely, when the enable signal ENABLE goes high, the state of the signal at the D input of the D-latch 44 at the start of each clock pulse is transferred to its Q output at the end of that clock pulse.

The Q output of the D-latch 44 is supplied to the analog gate 45 in order to control the operation thereof. The analog gate 45 is open, and thereby allows current to flow through the sensor 41, when the Q output of the D-latch 44 is high. In this state, the resistance of the analog gate 45 is substantially less than the load resistor 46. The current supplied to the sensor 41 is thus determined essentially by the values of the voltage V+ and of the resistor 46.

When the Q output of the D-latch 44 is low, the analog gate 45 remains closed and prevents the flow of current through the sensor 41. In this way, the operation of the analog gate 45 is controlled so that it remains either open or closed for at least the period of one clock cycle. It can be seen that the voltage V+ and the resistor 46 form a current source which is controlled by means of the analog gate 45 and the signal present at the Q output of the D-latch 44. The use of the D-latch 44 prevents the diagnostic circuit 40 from entering a race-around condition where the comparator output and the open/closed state of the analog gate oscillate rapidly back and forth and are thus ambiguous. It is to be appreciated that alternative means, such as an R-S flip-flop or other suitable circuit, may be used to control the operation of the current source's switching means.

The Q output of the D-latch 44 and the clock signal CLOCK are logically combined by the AND gate 49, whose output is connected to the counter 48. The counter 48 thus counts the number of clock cycles when the Q output of the D-latch is high. The output 50 of the counter 48 provides a binary number of the total time during which the Q output is in the logically high state. This total time is representative of the resistance of the sensor 41 as will become clear from the following. Other timing means for measuring the cumulative duration of the high state of the Q output will be apparent to one skilled in the art.

The operation of the diagnostic circuit 40 will now be explained with respect to FIG. 3, which shows a timing diagram of the clock signal CLOCK, the enable signal ENABLE, the Q output of the D-latch 44, the potential difference $V_{BS}$ across the sensor 41 and the D input of the D-latch 44 described in relation to FIG. 2. At a time $t_0$, the enable signal ENABLE goes from a low state to a high state. As the analog gate 45 is closed, no current flows through the sensor 41 and the potential difference $V_{BS}$ thereacross is zero volts. Under these conditions, the output of the comparator 42 is high.

At the end of the next clock pulse, at time $t_1$, the high state of the D input is transferred to the Q output, and the analog gate 45 conducts. Current is thus caused to flow through the resistor 46, the capacitor 47 and the sensor 41. As the current continues to flow, the capacitor 47 is charged and the potential difference $V_{BS}$ across the sensor 41 increase with time. For as long as this potential difference remains less than the reference voltage of 300 mV, the D input remains high, as does the Q output, and the analog gate 45 continues to conduct. In addition, during this time, the counter 48 counts the clock pulses transmitted to it by the AND gate 49.

In other embodiments of the present invention, the capacitor 47 may be omitted from the diagnostic circuit 40, the increase over time of the potential difference across the sensor 41 being due to the internal capacitance of the sensor itself.

At time $t_2$, the potential difference $V_{BS}$ across the sensor 41 reaches the value of 300 mV. The output of the comparator 42, and hence the D input, pass to the logically low level. At the end of the next clock pulse, at time t3, the Q output passes to the logically low level, thereby blocking the analog gate 45 and prevent current from flowing through the sensor 41. In addition, the AND gate 49 blocks the transmission of the clock pulses to the counter 48, which temporarily stops counting.

As current no longer flows from the voltage supply V+ and the resistor 46, the capacitor 47 discharges over time until, at a time $t_4$, the potential difference $V_{BS}$ across the sensor 41 falls to below the reference voltage of 300 mV. The comparator output and the D input therefore change from a low level to a high level. At the end of the next clock pulse, at time $t_5$, the Q output passes to a high level thereby causing the analog gate 45 to conduct and current to again flow through the resistance 46 and to the capacitor 47 and the sensor 41. The AND gate 49 is once again able to transmit the clock signal CLOCK to the counter 48, which recommences counting. The capacitor 47 is again charged by the current supplied via the voltage supply V+ and the resistor 46, so that the potential difference $V_{BS}$ across the sensor 41 again increases over time.

This process continues, the analog gate 45 passing alternatively between blocked state and its conducting state and vice-versa at the times $t_6$ to $t_{12}$ as represented in FIG. 3. The potential difference $V_{BS}$ across the sensor 41 thus oscillates around the value of 300 mV.

During the periods when the analog gate 45 conducts, the current $I_{BS}$ flowing in the resistor 46, after time $t_0$, is given by $$I_{BS}=(V+-V_{ref})/R_{46}$$

where $V_{ref}$ is the reference voltage of 300 mV and $R_{46}$ is the value of the resistor 46. This value $R_{46}$ is invariable, so that a constant current source is effectively provided for supplying a constant current to the sensor 41. The operation of this constant current source is controlled by the analog gate 45. In other embodiments of the invention, other realisations of a switchable constant current source may be used in place of that shown in FIG. 2, as will be appreciated by those skilled in the art. Further, the switching means for selectively operating the constant current source may be realised other than by the analog gate 45.

The proportion of time during which the analog gate 46 was open can be found by the ratio $^{NQ1}/_{(NQ1+NQ0)}$ where NQ1 is the total number of clock pulses which are counted by the counter 48 during the measurement time, this number NQ1 being thus representative of the total time during which the analog gate 45 was open over the measurement period and NQ0 is the number of clock pulses which were not counted by the counter 48 during the measurement period, this number NQ0 being representative of the total time during which the analog gate 45 was closed during the measurement time. The sum of the numbers NQ1 and NQ0 is obviously representative of the duration of the measurement period.

The mean current $I_{BS}$ave flowing to the sensor 41 and capacitor 47 is therefore given by $$I_{BS}ave=[(V+-V_{ref})/R_{46}]*[^{NQ1}/_{(NQ1+NQ0)}].$$

As the values of V+, $V_{ref}$, $R_{46}$ and (NQ1+NQ0) are predeterminable, the number NQ1 is representative of the mean current $I_{BS}$ave passing through the sensor 41 during the selected measurement interval.

Preferably, the diagnostic circuit 40 shown in FIG. 2 can be calibrated to account for possible variations in the value of constant current caused by a change in the value of V+ over time and/or any manufacturing variation in the value $R_{46}$ of the resistor 46. For example, if the voltage V+ is supplied by a power source such as a battery, it is known that the actual value of the voltage V+ will significantly fall over an extended period of time. Similarly, the precise value of the resistor 46 $R_{46}$ may vary from one circuit to the next by ±5% or more, depending upon manufacturing variations. Even though the absolute values V+ and $R_{46}$ may not be known with precision, they are nevertheless stable within a period of some hours. During a measurement period of some dozens of seconds, these values may be considered to be invariable.

In order to calibrate the diagnostic circuit 40 to eliminate the effect of the variation in the values of V+ and $R_{46}$, the sensor 41 may be replaced by a precision resistor 51 having a value $R_{cal}$. Such a resistor can be, for example, wirewound and have a tolerance of ±0.05% or better. The mean current $I_{cal}$ave flowing through the resistor 51 is given by $$I_{cal}ave=[(V+-V_{ref})/R_{46}]*[^{NQ1cal}/_{(NQ1cal+NQ0cal)}]$$

where NQ1cal is the total number of clock pulses counted while the analog gate 45 conducts during the measurement time and NQ0cal is number of clock pulses occuring while the analog gate 45 is blocked during the measurement time. From this it follows that $$(V+-V_{ref})/R_{46}=(V_{ref}*NQcal)/(R_{cal}*NQ1cal)=Xcal$$

where NQcal=(NQ1cal+NQ0cal) and Xcal is the calibration factor of the diagnostic circuit 40. As $V_{ref}$ and $R_{cal}$ are known, the calibration factor Xcal is obtainable directly from the output of the counter 48 for a selected measurement time corresponding to NQcal clock pulses.

After the determination of the calibration factor Xcal, the precision resistor 51 is replaced by the sensor 41 and the mean current $I_{BS}$ave flowing through the sensor 41 is measured as described above. The actual value of the resistance of the sensor 41 to which the binary number 50 corresponds is obtained by dividing the binary number 50 by the calibration factor Xcal. This can be understood by considering that the mean current $I_{BS}$ave flowing through the sensor 41 is given by $$I_{BS}ave=[(V+-V_{ref})/R_{46}]*(^{NQ1mes}/_{NQmes})=Xcal*(^{NQ1mes}/_{NQmes})$$

where NQ1mes is the number of clock pulses counted, once the precision resistor 51 has been replaced by the sensor 41, during the total time when the analog gate 45 conducts during the measurement time and NQ0mes is the corresponding number of clock pulses occuring when the analog gate 45 is blocked. The mean current $I_{BS}$ave passing through the sensor 41 may therefore be measured in a way which is independent of any variation in the values of V+ and $R_{46}$.

If the value $R_{46}$ of the resistor 46 is known with precision, the above-described calibration step, in which Xcal is determined, enables the actual value of V+ to additionally be determined from a calculation of $$V+=(Xcal*R_{46})-V_{ref}$$

which value may be used as a battery "end-of-life" detector to detect when the value V+ falls below a selected threshold, indicating that the battery should be replaced.

The diagnostic circuit 40 may also be used in applications requiring the measurement of temperature. An Negative-Temperature-Coefficient or NTC sensor, having a resistance which varies in a known way with temperature, may be used in place of the sensor 41. The binary number 50 at the output of the counter 48 in this case will be representative of the resistance of the NTC sensor and thus of the ambient temperature surrounding the NTC temperature.

Whilst the present invention has been described principally in relation to the measurement of blood glucose levels, the diagnostic circuit and method of amperometrically determining the current passing through a sensor using a diagnostic circuit of the present invention are also suitable for use in relation to the quantitative determination of other biologically important compounds such as TSH, T4, hormones such as HCG, cardiac glycosides such as Digoxin, antiarrhythmics such as Lidocaine, antiepileptics such as phenobarbital, antibiotics such as Gentamicin, cholesterol, non-therapeutic drugs and the like.

Finally, it is to be understood that various modifications and/or additions may be made to the diagnostic circuit and method of amperometrically determining the current passing through a sensor using a diagnostic circuit without departing from the ambit of the present invention as defined in the claims appended hereto.

What is claimed is:

1. Diagnostic circuit for amperometrically determining the current passing through a sensor (41), comprising a current source (V+, 46) for passing a constant DC current through said sensor (41), switching means (45) for selectively operating said current source, comparing means (42) for comparing the potential difference ($V_{BS}$) across said sensor to a reference voltage ($V_{ref}$), and producing a control signal (D) having a first logic level when said potential difference is less than said reference voltage ($V_{ref}$) and a second logic level when said potential difference is greater than said reference voltage ($V_{ref}$), control means (44) for providing a switching signal (Q) having said first logic level in response to said control signal (D) having said first logic level and said second logic level in response to said control signal (D) having said second logic level, said switching means (45) being caused to operate when said switching signal (Q) is in said first logic level, and timing means (48,49) for measuring the cumulative time during which said switching signal (Q) has said first logic level during a selected time interval, so as to provide an output signal (50) indicative of a mean value of current ($I_{bs}$ave) passing through said sensor (41).

2. Diagnostic circuit according to claim 1, said control means comprising
a clock signal (CLOCK) having a known number of cycles per second,
a latching circuit (44) for maintaining the logic level of said switching signal (Q) during each clock cycle, said timing means comprising
a counting circuit (48) for counting the number of cycles during which said switching signal (Q) has said first logic level during said time interval.

3. A method of amperometrically determining the current passing through a sensor using the diagnostic circuit according to claim 2, said method comprising the following steps:

(a) replacing said sensor (41) with a calibration element (51) of known resistance, (b) measuring a first cumulative time (NQ1cal) during which said switching signal (Q) is at said first logic level during said time interval so as to determine a calibration factor (Xcal), (c) replacing said calibration element (51) with said sensor (41), (d) measuring a second cumulative time (NQ1mes) during which said switching signal is at said first logic level during said time interval, and (e) multiplying said second cumulative time (NQ1mes) by said calibration factor (Xcal) so as to provide an output signal indicative of the mean current ($l_{bs}$ave) passing through the sensor (41) during said time interval.

4. The method according to claim 3, wherein steps (b) and (d) comprise counting the number of cycles, during said time interval, when said switching signal (Q) is in said first logic level.

5. Diagnostic circuit according to claim 2, said current source comprising a voltage source (V+) for supplying a constant DC voltage, a resistance element (46) connected between said voltage source (v+) and said sensor (41), said switching means (45) being selectively operated so as to maintain the potential difference across said sensor (41) at a substantially constant level and thus supply a substantially constant DC current ($I_{BS}$) to said sensor (41) when said switching means (45) is operated.

6. Diagnostic circuit according to claim 5, and further comprising a capacitive element (47) connected in parallel with said sensor (41).

7. Diagnostic circuit according to claim 5, wherein said switching means (45) is connected in series with said resistance element (46).

8. Diagnostic circuit according to claim 7, wherein said switching means (45) has a resistance substantially less than said resistance element (46).

9. Diagnostic circuit according to claim 1, wherein said control means comprises a D-latch (44) having a D input and a Q output, said control signal being supplied to said D input and said switching signal being supplied by said Q output.

10. Diagnostic circuit according to claim 9, wherein said timing means (48,49) counts the number of clock cycles, during said time interval, when said Q output is at said first logic level.

11. A method of amperometrically determining the current passing through a sensor using the diagnostic circuit according to claim 10, said method comprising the following steps:

(a) replacing said sensor (41) with a calibration element (51) of known resistance, (b) measuring a first cumulative time (NQ1cal) during which said switching signal (Q) is at said first logic level during said time interval so as to determine a calibration factor (Xcal), (c) replacing said calibration element (51) with said sensor (41), (d) measuring a second cumulative time (NQ1mes) during which said switching signal is at said first logic level during said time interval, and (e) multiplying said second cumulative time (NQ1mes) by said calibration factor (Xcal) so as to provide an output signal indicative of the mean current ($I_{b_s}$ave) passing through the sensor (41) during said time interval.

12. The method according to claim 11, wherein steps (b) and (d) comprise counting the number of clock cycles during which said Q output is in said first logic level during said time interval.

13. A method of amperometrically determining the current passing through a sensor using a diagnostic circuit according to claim 1, said method comprising the following steps:

(a) replacing said sensor (41) with a calibration element (51) of known resistance, (b) measuring a first cumulative time (NQ1cal) during which said switching signal (Q) is at said first logic level during said time interval so as to determine a calibration factor (Xcal), (c) replacing said calibration element (51) with said sensor (41), (d) measuring a second cumulative time (NQ1mes) during which said switching signal is at said first logic level during said time interval, (e) multiplying said second cumulative time (NQ1mes) by said calibration factor (Xcal) so as to provide an output signal indicative of the mean current ($I_{b_s}$ave) passing through said sensor (41) during said time interval.

* * * * *